United States Patent

Koshiba

(10) Patent No.: US 10,091,480 B2
(45) Date of Patent: Oct. 2, 2018

(54) DRIVING METHOD OF IMAGING ELEMENT, IMAGING DEVICE WITH READ-OUT TIME AND ACCUMULATION PERIOD

(71) Applicant: FUJIFILM Corporation, Tokyo (JP)

(72) Inventor: Masaaki Koshiba, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 169 days.

(21) Appl. No.: 14/497,500

(22) Filed: Sep. 26, 2014

(65) Prior Publication Data

US 2015/0092036 A1 Apr. 2, 2015

(30) Foreign Application Priority Data

Sep. 27, 2013 (JP) ................. 2013-201251

(51) Int. Cl.
*H04N 7/18* (2006.01)
*H04N 9/77* (2006.01)
*H04N 5/353* (2011.01)
*H04N 5/355* (2011.01)
*A61B 1/00* (2006.01)
(Continued)

(52) U.S. Cl.
CPC .......... *H04N 9/77* (2013.01); *A61B 1/00006* (2013.01); *A61B 1/00009* (2013.01); *A61B 1/05* (2013.01); *A61B 1/0669* (2013.01); *A61B 1/07* (2013.01); *H04N 5/3535* (2013.01); *H04N 5/35554* (2013.01); *H04N 5/378* (2013.01); *H04N 9/045* (2013.01)

(58) Field of Classification Search
CPC ...................................... H04N 9/77
USPC ........................................ 348/71
See application file for complete search history.

(56) References Cited

U.S. PATENT DOCUMENTS 7,750,278 B2 7/2010 Oike et al.
8,368,771 B2 2/2013 Kino
(Continued)

FOREIGN PATENT DOCUMENTS

EP 2 523 452 A1 11/2012
EP 2 604 176 A1 6/2013
(Continued)

OTHER PUBLICATIONS

European Office Action dated Jul. 20, 2016 in corrseponding European Patent Application 14 186 400.9.
(Continued)

*Primary Examiner* — Richard Torrente
(74) *Attorney, Agent, or Firm* — Birch, Stewart, Kolasch & Birch, LLP

(57) ABSTRACT

It is a method of driving a MOS type imaging element in which pixels having sensitivities for different colors are arranged two-dimensionally, in which the imaging element has at least two types of read-out lines having different pixel arrangements to read out a charge signal of the pixels, and the method includes driving such that a read-out time interval of a charge signal of at least one type of read-out line among the read-out lines is longer than a read-out time interval of another type of read-out line and a charge accumulating period of each pixel of the one type of read-out line is longer than a charge accumulating period of each pixel of said another type of read-out line.

11 Claims, 22 Drawing Sheets

(51) Int. Cl.
*A61B 1/05* (2006.01)
*H04N 5/378* (2011.01)
*H04N 9/04* (2006.01)
*A61B 1/06* (2006.01)
*A61B 1/07* (2006.01)

(56) References Cited

U.S. PATENT DOCUMENTS

| | | |
|---|---|---|
| 8,643,710 B2 | 2/2014 | Ono et al. |
| 2005/0231618 A1 | 10/2005 | Sugiyama |
| 2008/0173794 A1 | 7/2008 | Oike et al. |
| 2010/0253833 A1 | 10/2010 | Deever et al. |
| 2011/0149106 A1 | 6/2011 | Kino |
| 2012/0274822 A1* | 11/2012 | Smith ............... H04N 5/23254 348/302 |
| 2013/0169843 A1* | 7/2013 | Ono ................... A61B 1/045 348/234 |
| 2013/0245410 A1 | 9/2013 | Saito |
| 2013/0308044 A1 | 11/2013 | Mitsunaga |
| 2014/0152790 A1* | 6/2014 | Saito ................... A61B 1/0005 348/68 |
| 2014/0232929 A1 | 8/2014 | Ichikawa |

FOREIGN PATENT DOCUMENTS

| | | |
|---|---|---|
| JP | 2005-295381 A | 10/2005 |
| JP | 2007-214832 A | 8/2007 |
| JP | 2009-194604 A | 8/2009 |
| JP | 2011-151795 A | 8/2011 |
| JP | 2012-175234 A | 9/2012 |
| JP | 2013-188365 A | 9/2013 |
| WO | WO 2012/043771 A1 | 4/2012 |

OTHER PUBLICATIONS

Japanese Office Action, dated Aug. 18, 2015, for Japanese Application No. 2013-201251, together with an English translation thereof.
Summons to Attend Oral Proceedings issued on Feb. 9, 2017 in corresponding European Patent Application No. 14186400.9.
Extended European Search Report, dated May 15, 2015, in related application No. EP14186400.9.

* cited by examiner

FIG. 7

|  | R | Gr | Gb | B |
|---|---|---|---|---|
| FRAME 1 | R1 | Gr1 | Gb1 | B1 |
| FRAME 2 | R2 | Gr2 | Gb1 | B1 |
| FRAME 3 | R3 | Gr3 | Gb3 | B3 |
| FRAME 4 | R4 | Gr4 | Gb3 | B3 |
| ⋮ | ⋮ | ⋮ | ⋮ | ⋮ |

*FIG. 10*

|  | R | Gr | Gb | B |
|---|---|---|---|---|
| FRAME 1 | R1 ×α | Gr1 ×α | Gb1 | B1 |
| FRAME 2 | R2 ×α | Gr2 ×α | Gb1 | B1 |
| FRAME 3 | R3 ×α | Gr3 ×α | Gb3 | B3 |
| FRAME 4 | R4 ×α | Gr4 ×α | Gb3 | B3 |
| ⋮ | ⋮ | ⋮ | ⋮ | ⋮ |

FIG. 13

| | R | Gr | Gb | B |
|---|---|---|---|---|
| FRAME 1 | R1　R2　AVERAGE | Gr1　Gr2　AVERAGE | Gb1 | B1 |
| FRAME 2 | R3　R4　AVERAGE | Gr3　Gr4　AVERAGE | Gb2 | B2 |
| FRAME 3 | R5　R6　AVERAGE | Gr5　Gr6　AVERAGE | Gb3 | B3 |
| ⋮ | ⋮ | ⋮ | ⋮ | ⋮ |

*FIG. 22*

|         | R   | G   | B   |
|---------|-----|-----|-----|
| FRAME 1 | R₁  | Gr₁ | —   |
| FRAME 2 | —   | —   | B₂  |
| FRAME 3 | R₂  | Gr₂ | —   |
| FRAME 4 | —   | —   | B₄  |
| ⋮       | ⋮   | ⋮   | ⋮   | ns, sufficient sensitivity may
DRIVING METHOD OF IMAGING ELEMENT, IMAGING DEVICE WITH READ-OUT TIME AND ACCUMULATION PERIOD

CROSS-REFERENCE TO RELATED APPLICATIONS

This application is based on and claims priority under 35 USC 119 from Japanese Patent Application No. 2013-201251 filed on Sep. 27, 2013, the entire content of which is incorporated herein by reference.

BACKGROUND

1. Technical Field

The present invention relates to a driving method of an imaging element, an imaging device, and an endoscopic device.

2. Related Art

An imaging element which generates an image signal of an imaged observed image is inserted in a device having an imaging function, such as a digital camera, a video camera, or a portable phone. A technology for achieving high sensitivity or high density of a pixel of the imaging element as compared with the related art is being developed and in recent years, various technologies such as a technology which increases color reproducibility of a subject or a technology which expands a dynamic range have been proposed (see, Patent Literature 1 (JP-A-2009-194604) and Patent Literature 2 (JP-A-2012-175234)).

Further, the imaging element is also used in the medical field, and is mounted in, for example, a tip end of an insertion portion of an endoscope of the endoscopic device which is inserted in a body cavity.

SUMMARY OF INVENTION

However, when the imaging element is driven to capture a moving image at a frame rate of 30 fps or 60 fps, a charge accumulating period of each pixel is shortened as the frame rate is increased. The charge accumulating period is at most 1/30 seconds at 30 fps and 1/60 seconds at 60 fps. Therefore, in some observation conditions, sufficient sensitivity may not be obtained and only a dark and blurred moving image may be obtained.

For example, a highly sensitive imaging element is demanded in an endoscopic device which images a dark body cavity, since the observation is performed in a living body and thus, it may be difficult to sufficiently increase an intensity of illumination light.

An observation mode by the endoscopic device includes a normal observation mode in which white light is irradiated to perform observation and a narrow band light observation mode in which blue narrow band light is irradiated onto a subject to emphasize and observe a capillary vessel or a microstructural pattern of a superficial layer of a living tissue. Although the narrow band light observation mode is intended to exactly detect a blue reflective light from the subject, the blue reflective light is weak and a light quantity thereof tends to be insufficient as compared with the normal observation mode. Further, since a light transmission rate of a color filter of the imaging element is low, the observation image is dark and noise of the image signal is increased. Under this situation, it is difficult to obtain a moving image having sufficient brightness suitable for diagnosis.

Therefore, the present invention has been made in an effort to provide a driving method of an imaging element, an imaging device, and an endoscopic device which may generate an image which is always bright and has reduced noise even if an imaging signal of a subject is weak.

(1) According to an aspect of the present invention, it is a method of driving a MOS type imaging element in which pixels having sensitivities for different colors are arranged two-dimensionally, wherein the imaging element has at least two types of read-out lines having different pixel arrangements to read out a charge signal of the pixels, and the method comprises driving such that a read-out time interval of a charge signal of at least one type of read-out line among the read-out lines is longer than a read-out time interval of another type of read-out line and a charge accumulating period of each pixel of the one type of read-out line is longer than a charge accumulating period of each pixel of said another type of read-out line.

(2) According to another aspect of the present invention, it is an imaging device comprising: a MOS type imaging element in which pixels having sensitivities for different colors are arranged two-dimensionally; and a driving control unit which drives the imaging element by the driving method of the imaging element of (1).

(3) According to another aspect of the present invention, it is an endoscopic device, comprising the imaging device of (2).

According to any aspect of the driving method of imaging element, the imaging device and the endoscopic device, an image which is always bright and has reduced noise even can be generated even when an imaging signal of a subject is weak.

BRIEF DESCRIPTION OF DRAWINGS

FIG. 7 is an explanatory view illustrating contents of RGB image signals in a moving image which is generated from image information illustrated in FIG. 6.

FIG. 10 is an explanatory view illustrating driving to match brightness levels in image signals of a pixel of an RG line whose exposure time is short and a pixel of a GB line whose exposure time is long.

FIG. 13 is an explanatory view illustrating contents of a moving image which is generated by information on a charge signal obtained from a driving pattern of FIG. 12.

FIG. 22 is an explanatory view illustrating contents of R, G, and B signals to calculate information of a blood volume and an oxygen saturation level of blood hemoglobin of a subject which is obtained from image information illustrated in FIG. 21.

DESCRIPTION OF EMBODIMENTS

Hereinafter, an embodiment of the present invention will be described in detail with reference to the drawings.

Here, an imaging element which is mounted in an endoscopic device is described as an example of an imaging element, but the imaging element may be mounted in an imaging device having other photographing functions such as a digital camera and a video camera, in addition to the endoscopic device.

<Configuration of Endoscopic Device>

Figure 1:
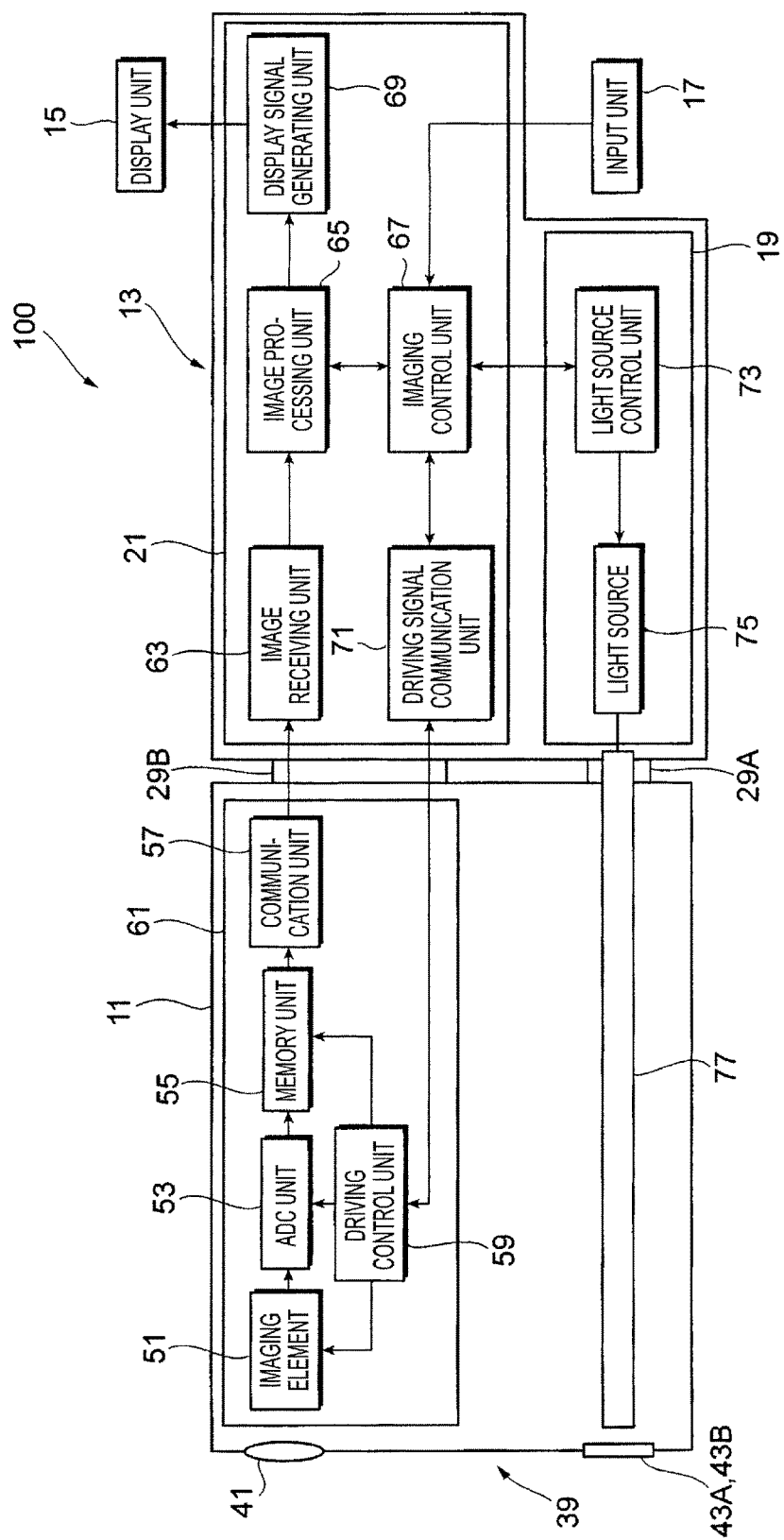
FIG. 1 is a view for illustrating an embodiment of the present invention and is a block diagram of an endoscopic device.
Figure 2:
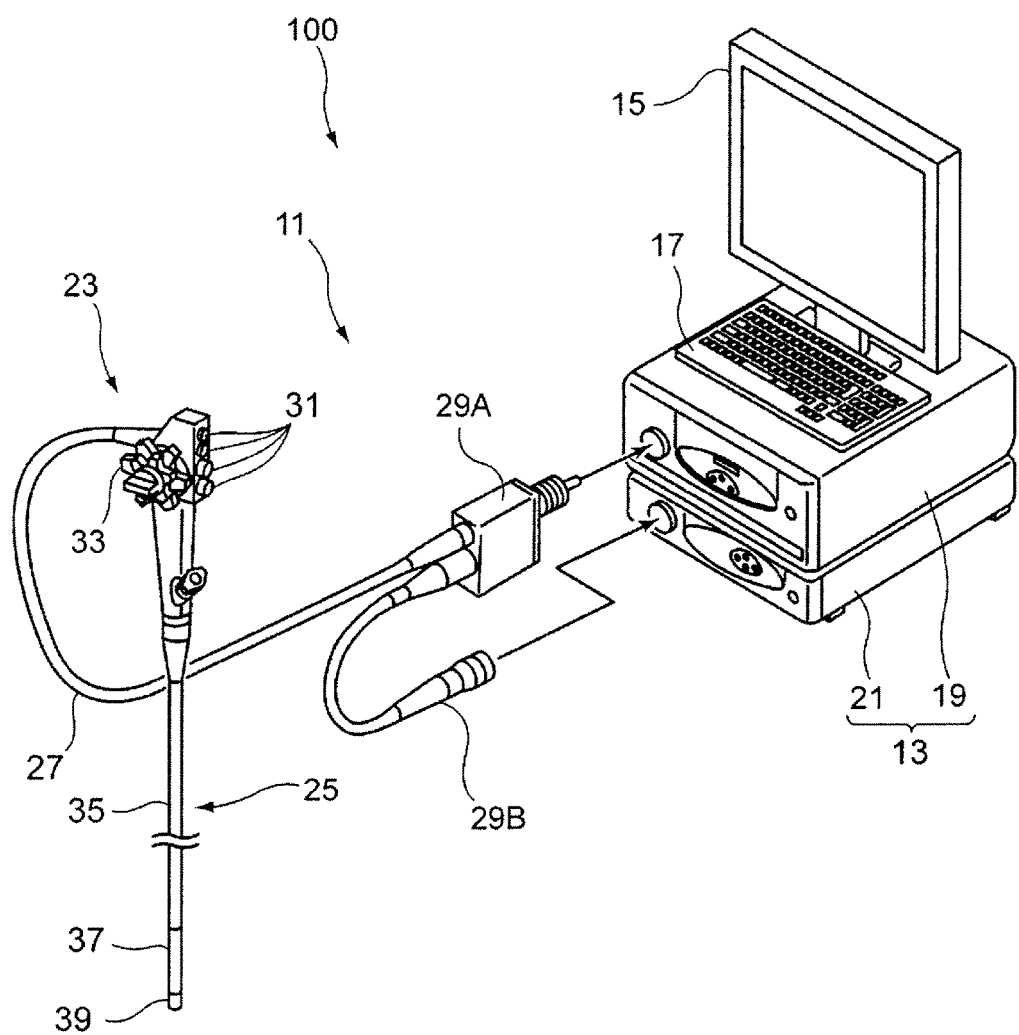
FIG. 2 is an appearance view illustrating a specific exemplary configuration of an endoscopic device.

FIG. 1 is a diagram illustrating an embodiment of the present invention and is a block diagram of an endoscopic device and FIG. 2 is an appearance diagram illustrating a specific exemplary configuration of an endoscopic device.

As illustrated in FIG. 1, an endoscopic device 100 includes an endoscopic scope 11, a control device 13, a display unit 15, and an input unit 17 which inputs information to the control device 13, such as a key board or a mouse. The control device 13 is configured by a light source device 19 which outputs illumination light and a processor 21 which performs a signal processing of an observation image.

The endoscopic scope 11, as illustrated in FIG. 2, includes a main body operating unit 23, an endoscopic insertion unit 25 which is connected to the main body operating unit 23 to be inserted into a subject (a body cavity) and an universal cord 27 which connects the main body operating unit 23 and the control device 13. A light guide LG connector 29A connected to the light source device 19 and a video connector 29B connected to the processor 21 are provided at a tip end of the universal cord 27.

In the main body operating unit 23 of the endoscopic scope 11, various operation input units 31 including buttons which perform suction, air supplying, and water feeding at a tip of the insertion unit 25, a shutter button at the time of imaging, and a mode switching button which switches observation modes are provided consecutively. Further, a pair of angle knobs 33 are provided in the main body operating unit 23.

The insertion unit 25 is configured by a flexible portion 35, a curved portion 37, and a tip end (an endoscopic tip end) 39 in this order from the main body operating unit 23. The curved portion 37 is remotely operated to be curved by rotating the angle knob 33 of the main body operating unit 23. Therefore, the endoscopic tip end 39 is directed to a desired direction.

Figure 3:
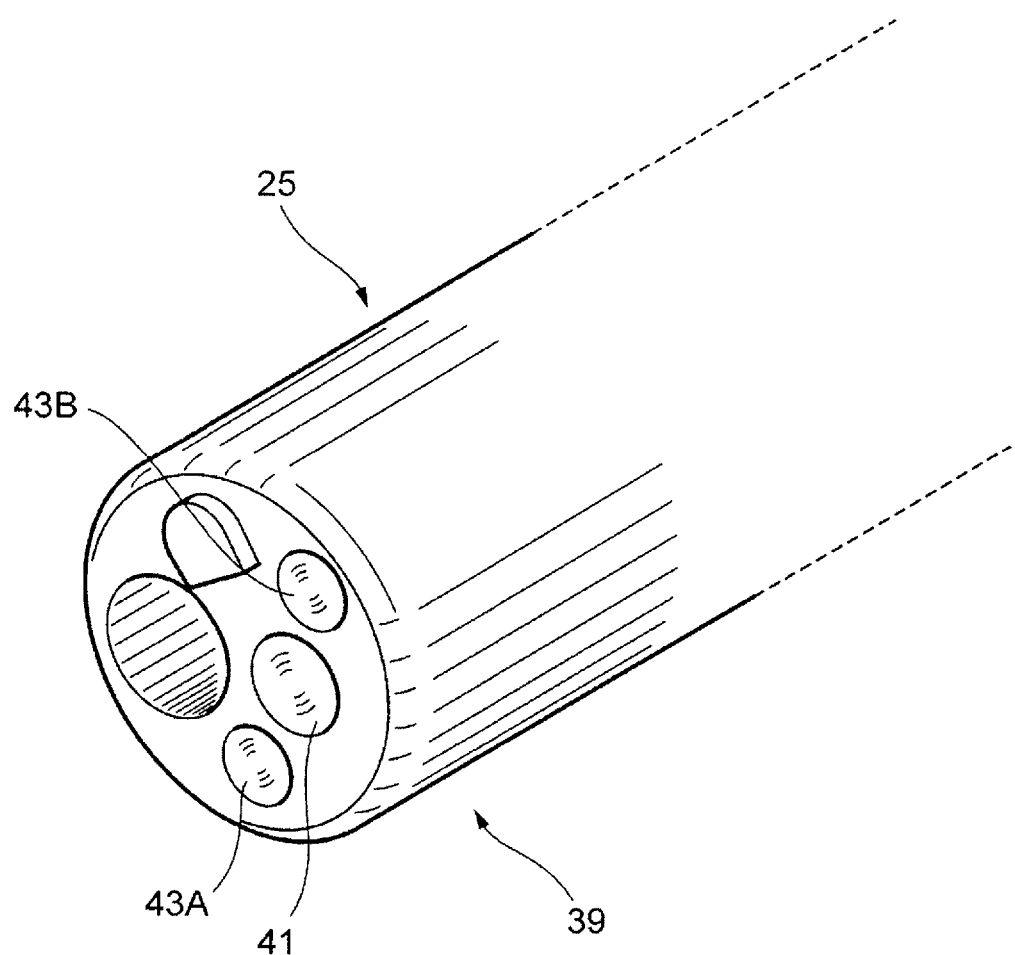
FIG. 3 is an enlarged perspective view of a tip end of an endoscope.

FIG. 3 illustrates an enlarged perspective view of an endoscopic tip end. In the endoscopic tip end 39, an observation window 41 of an imaging optical system and illumination windows 43A and 43B of an illumination optical system are disposed. Each illumination window 43A and 43B emits illumination light onto the subject. Reflective light from the subject is detected (imaged) by an imaging element through the observation window 41.

As illustrated in FIG. 1, an imaging optical system of an endoscopic scope 11 includes the observation window 41, the imaging element 51, an analog/digital converter (ADC unit) 53, a memory unit 55, a communication unit 57, and a driving control unit 59. Further, although not illustrated, an optical member such as a lens which focuses an observation image onto the imaging element 51 is disposed between the observation window 41 and the imaging element 51. The imaging element 51, the ADC unit 53, the memory unit 55, the communication unit 57, and the driving control unit 59 configure an imaging unit 61.

The control device 13 includes an image receiving unit 63, an image processing unit 65, an imaging control unit 67, a display signal generating unit 69, and a driving signal communication unit 71.

The light source device 19 includes a light source control unit 73 and a light source 75 and configures the illumination optical system together with the light guide 77 and the above-mentioned illumination windows 43A and 43B.

The imaging element 51 is a CMOS (Complementary Metal Oxide Semiconductor) type imaging element in which pixels having sensitivities for a plurality of different colors are two-dimensionally arranged. Although descriptions are made herein assuming that the imaging element 51 includes color filters having primary colors of RGB, the imaging element 51 may include color filters having complementary colors such as CMY or CMYG.

Figure 4:
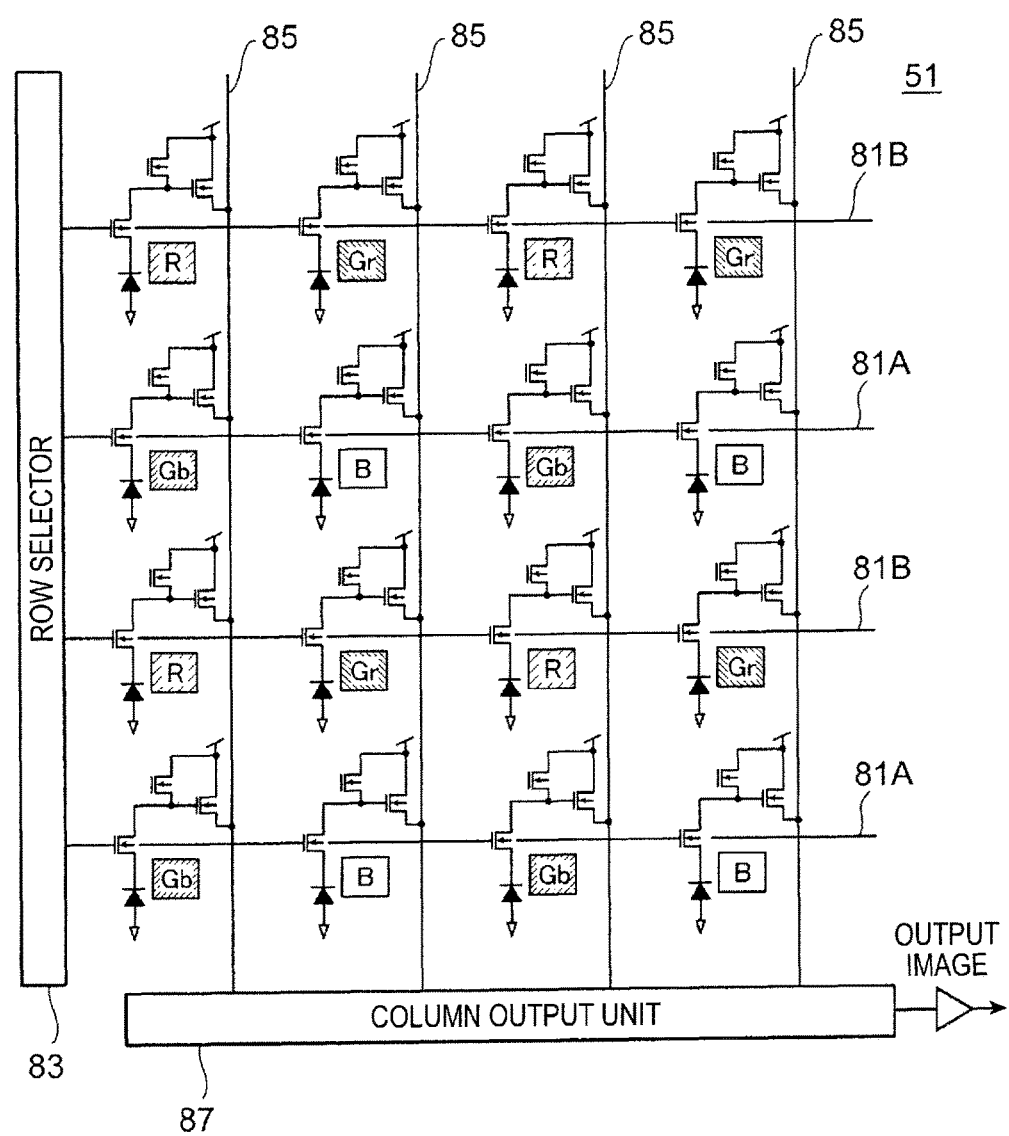
FIG. 4 is an explanatory view schematically illustrating a part of a configuration of an imaging element.

FIG. 4 is an explanatory view schematically illustrating a part of configuration of an imaging element. Squares in the drawing respectively represent pixels which are two-dimensionally arranged on an imaging surface. Lines serving as read-out lines which perform read-out of a charge signal (hereinafter, also referred to as an "image signal") of an accumulated charge are represented as control lines which extend in a horizontal direction in the drawing and include two types of lines which include pixels having different color sensitivities. Further, although the lines are arranged in a Bayer pattern in the illustrated example, the arrangement of the color filters is not limited thereto.

The read-out lines include a first read-out line 81A in which pixels Gb having a sensitivity for a green light and pixels B having a sensitivity for a blue light are repeatedly arranged and a second read-out line 81B in which pixels R having a sensitivity for a red light and pixels Gr having a sensitivity for a green light are repeatedly arranged.

The ADC unit 53 converts an image signal input from the imaging element 51 into digital data. Further, the ADC unit 53 adjusts a gain if necessary. The memory unit 55 temporarily stores the digital data output from the ADC unit and outputs the digital data to the communication unit 57. The communication unit 57 converts the digital data into a signal type which is appropriate for communication, such as a serial signal, and outputs the signal to the processor 21. The driving control unit 59 connected to the imaging element 51, the ADC unit 53, and the memory unit 55 has a timing generator and drives and controls the units.

The communication unit 57 outputs a signal of the digital data to the image receiving unit 63 of the processor 21. The image receiving unit 63 outputs the input signal to the image processing unit 65. The image processing unit 65 receives a command from the imaging control unit 67 to process the received signal as an image and output the image to the display signal generating unit 69. The display signal generating unit 69 converts a received display signal into an image signal such as a video signal to output the image signal to the display unit 15 so that an image is displayed on the display unit 15.

The driving control unit 59 changes imaging conditions of the imaging element 51 such as read-out of a charge signal, a shutter speed, and signal amplification in accordance with the command from the imaging control unit 67 and drives the imaging element 51.

The imaging control unit 67 outputs an imaging driving signal which changes the imaging condition of the imaging element 51 in accordance with the input image signal to the driving signal communication unit 71. The driving signal communication unit 71 outputs the imaging driving signal to the driving control unit 59 and changes the imaging condition of the imaging unit 61 if necessary. Further, the imaging control unit 67 drives the light source device 19 in accordance with the input image signal. The imaging control unit 67 instructs a lighting timing or an emission light amount by outputting an illumination light driving signal to the light source control unit.

Upon receiving the driving signal from the light source control unit 73, the light source 75 is driven and turned on and simultaneously emits emission light from the illumination windows 43A and 43B of the endoscopic tip end 39 through a light guide 77 which is a light guiding member. The light source 75 is a white light source but may be a light source formed by combining a white light source and a light source of special light which emits a blue narrow band light. As for the blue narrow band light, for example, a light having a center wavelength of 400 nm to 450 nm from a laser light source or an LED light source may be used. Further, the blue narrow band light may be extracted by selecting a wavelength of broad wavelength light from a white light source such as a xenon lamp or a halogen lamp using an optical filter.

<Driving Method of Imaging Element>

Next, a driving method of an imaging element 51 will be described.

As illustrated in FIG. 4, read-out lines 81A and 81B are connected to a row selector 83 and driving signals from the row selector 83 are output to the pixels. Further, control lines 85 in a vertical direction are connected to a column output unit 87 which includes a column selector. The charge signal of each pixel is taken into the column output unit 87 by driving the column selector.

The row selector 83 and the column selector of the column output unit 87 are connected to the driving control unit 59 illustrated in FIG. 1 and are driven by a driving signal for the imaging element 51. The row selector 83 and the column output unit 87 receive the driving signal and output the charge signal of each pixel through the column output unit 87 as an image signal. A basic configuration for outputting the image signal is the same as a known configuration for an ordinary CMOS imaging element.

First Control Example

Figure 5:
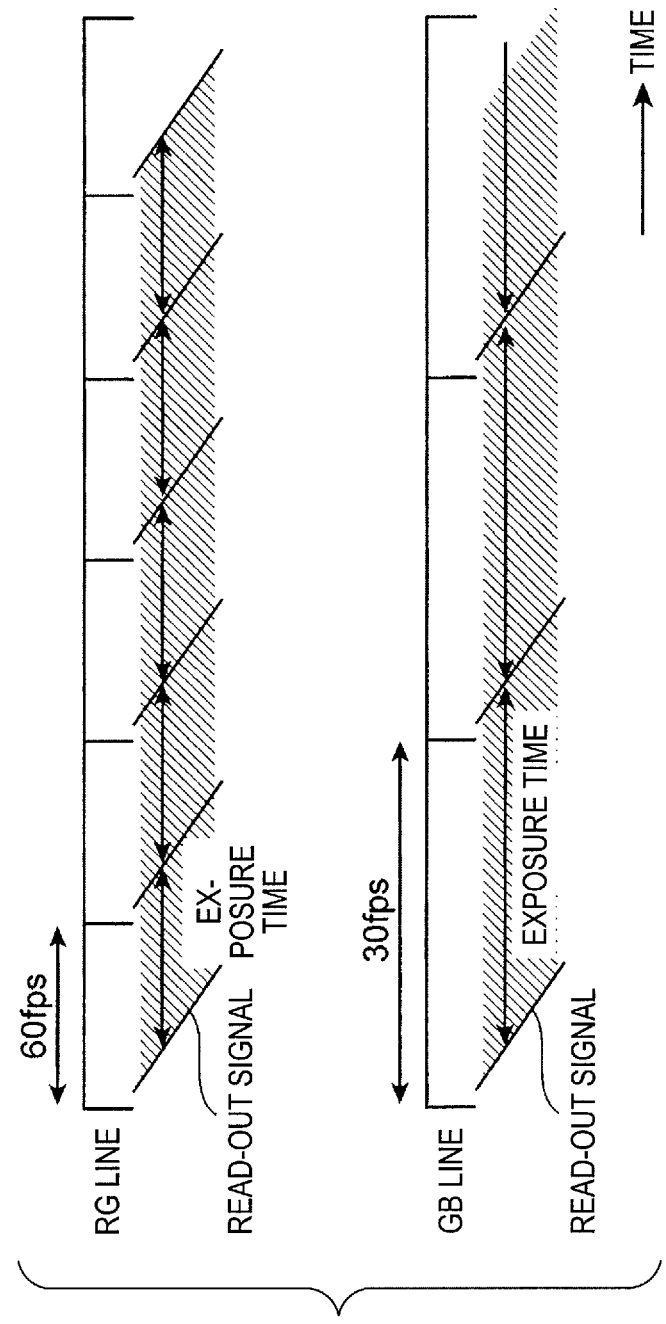
FIG. 5 is an explanatory view illustrating a read-out driving pattern of a charge signal.

FIG. 5 is an explanatory view illustrating a first read-out driving pattern of a charge signal. In the driving pattern, read-out rates which indicate read out time intervals vary in a GB line corresponding to the first read-out line 81A and a RG line corresponding to the second read-out line 81B, illustrated in FIG. 4. Further, the charge accumulating period (hereinafter, simply referred to as an "exposure time") of the pixels of each line varies in the BG line and in the RG line so that the charge accumulating period of the BG line is longer than the charge accumulating period of the RG line.

In the illustrated example, the row selector 83 outputs read-out signals at 60 fps in the RG line and sequentially sets the RG lines as read-out lines to perform a read-out operation. Further, in the GB line, the row selector 83 outputs read-out signals in synchronization with read out signals per every two commas by the RG line (that is, at 30 fps) and sequentially sets the BG lines as read-out lines to perform the read-out operation. That is, the read-out and the reset are performed on the RG line one time for 1/60 seconds and on the GB line one time for 1/30 seconds. Therefore, the exposure time of the GB line is twice as long as the exposure time of the RG line.

Figure 6:
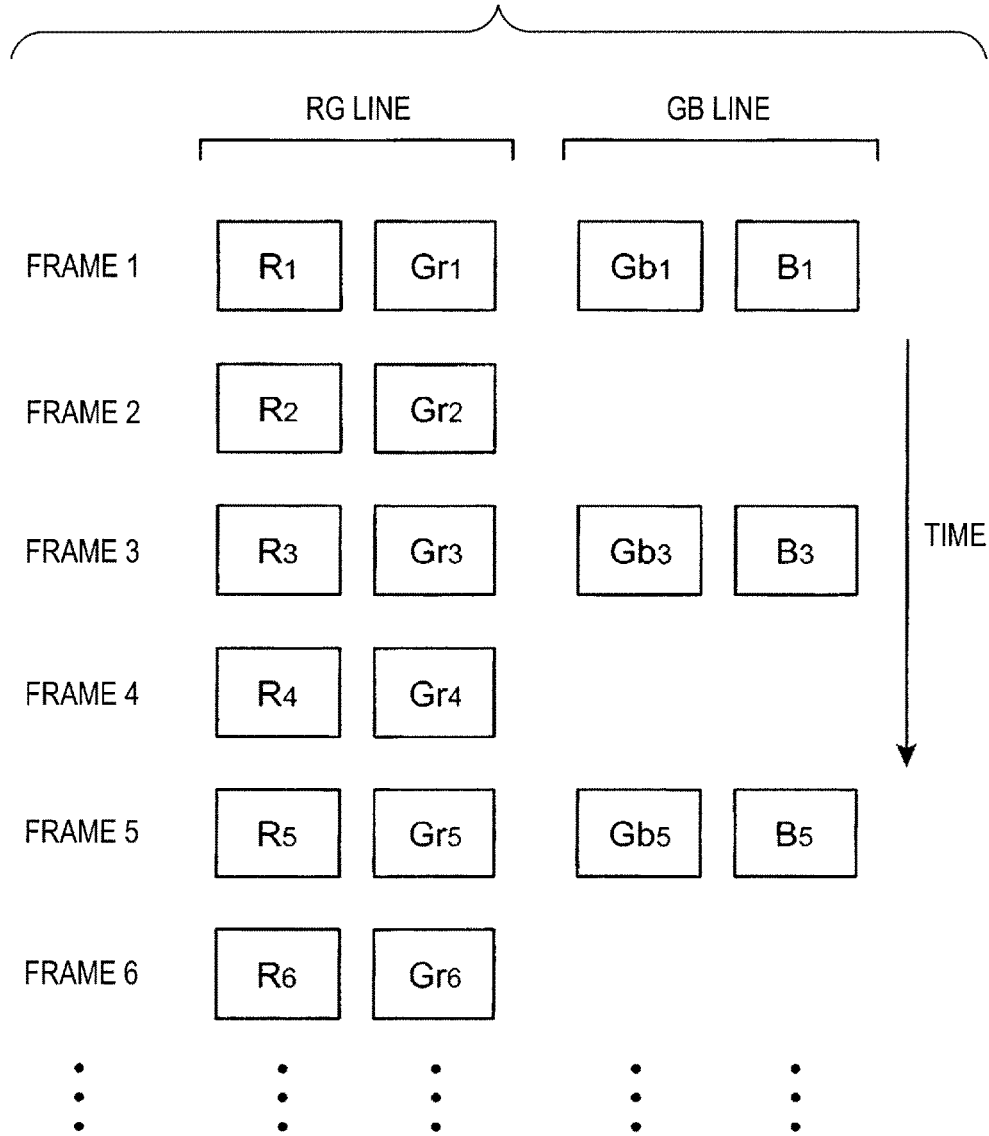
FIG. 6 is an explanatory view illustrating transition of image information obtained by the driving pattern.

Transition of the image information obtained by the driving pattern is schematically illustrated in FIG. 6. In FIG. 6, an image signal from a pixel R obtained during a period of Frame 1 is denoted by R1, an image signal from a pixel Gr is denoted by Gr1, an image signal from a pixel Gb is denoted by Gb1, and an image signal from a pixel B is denoted by B1, and the same pattern is applied to subsequent frames.

During the period of Frame 1, the image signals R1 and Gr1 of the RG line and the image signals Gb1 and B1 of the GB line may be obtained. During a period of Frame 2, only image signals R2 and Gr2 of the RG line are obtained and the image signals of the pixel Gb and the pixel B are not obtained because the pixels are being exposed. During a period of Frame 3, image signals R3 and Gr3 of the RG line and image signals Gb3 and B3 of the GB line may be obtained.

A frame mentioned herein is one still image (one coma) in a moving image and for a brief description, it is assumed that an image signal of a frame n (n is an integer) refers to an image signal when an image signal read out from each pixel in a period of each frame is temporally stored in a memory and the stored image signal is read out in a post processing to build a frame image. That is, the above-mentioned image signals R1 and Gr1 are image signals based on a charge accumulated in the preceding frame period and the above-mentioned image signals Gb1 and B1 are image signals based on a charge accumulated in the preceding frame period and the frame period before the preceding frame period.

FIG. 7 illustrates contents of RGB image signals in a moving image which is generated from image information illustrated in FIG. 6. In the moving image illustrated in FIG. 7 as an example, frame images are generated by the image signals R1, Gr1, Gb1, and B1 in the period of Frame 1. Further, in this case, a gain of the image signal Gb1 is corrected in accordance with a difference of an exposure time. In the period of Frame 2, although the image signals R2 and Gr2 may be obtained, an image signal of the pixel B is not obtained due to a difference of read-out rates of the charge signals. Therefore, a frame image is generated by substituting the image signals Gb1 and B1 of Frame 1. During the period of Frame 3, a frame image is generated by the image signals R3, Gr3, Gb3, and B3. In this case, the image is formed while compensating for information on different exposure timings so that an image quality of the moving image may be further improved.

As for the signals Gr and Gb in FIG. 7, if necessary, an image signal of a pixel Gr may be supplemented with an image signal of a pixel Gb or an image signal of the pixel Gb may be supplemented with an image signal of the pixel Gr.

Figure 8:
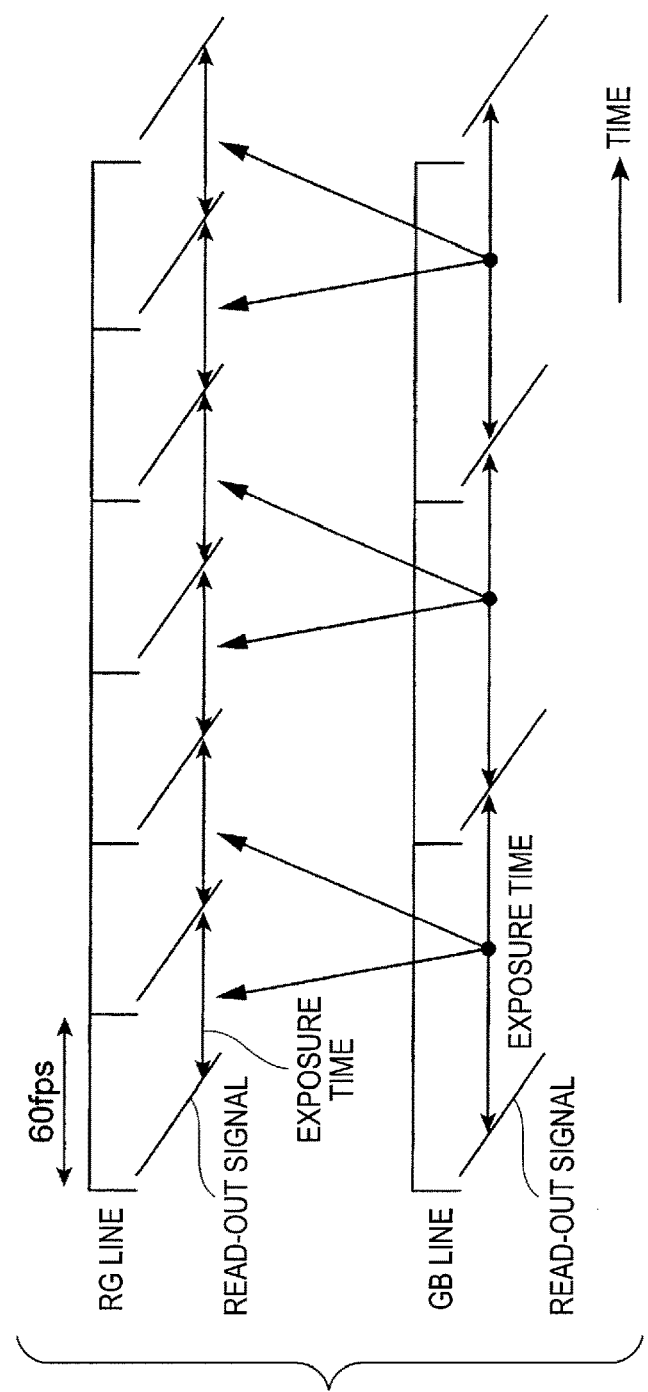
FIG. 8 is an explanatory view illustrating a read-out pattern of a charge signal.

According to this driving pattern, as illustrated in FIG. 8 as an explanatory view of a read out pattern of the charge signal, an image signal which is read out from the GB line is commonly used for image signals for two comas which are read out from the RG line. That is, the frame of the GB line is updated one time for a period of two consecutive comas in a time axis of the RG line so that a moving image of 60 fps may be generated.

According to the driving pattern, an exposure time of a pixel in the GB line is longer than an exposure time of a pixel in the RG line so that sensitivity of detecting a pixel of the GB line may be improved. Therefore, in normal observation by an endoscopic device which uses a white light, sensitivity of a blue reflective light is increased as compared with a red reflective light and a green reflective light so that an observation image in which a blue reflective light component is emphasized may be obtained. Further, when narrow band light observation of the blue light is performed by the endoscopic device, detecting sensitivity for a weak blue reflective light from the subject is improved so that a sharper vessel-emphasized image may be obtained.

Second Control Example

Figure 9:
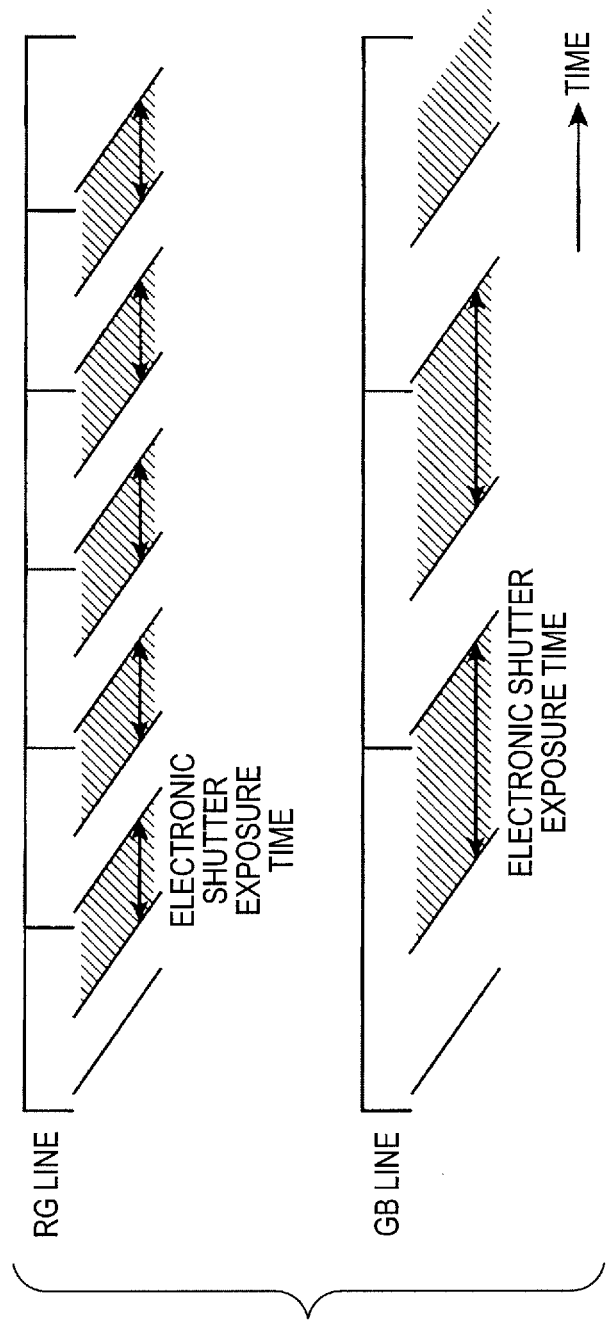
FIG. 9 is an explanatory view illustrating a second read-out driving pattern of a charge signal.

In the first driving pattern illustrated in FIG. 5, the exposure time of each pixel is a time from a read-out timing of a charge signal to the next read-out timing but in this driving example, the exposure time is changed using an electronic shutter. FIG. 9 illustrates an explanatory view of a second read-out driving pattern of a charge signal. In the second driving pattern, the exposure time of each pixel is set as a shutter open period of the electronic shutter.

According to this driving pattern, the exposure times of the pixels of the GB line and the RG line may be independently and arbitrarily changed using the electronic shutter. Therefore, the exposure time of each of the pixels of the GB line is simply set as arbitrary multiples of the exposure time of each of the pixels of the RG line or a ratio of the exposure times of the respective pixels of the GB line and the RG line is simply adjusted to be constant at all times. Further, a pulse light is used as the illumination light or a mechanical shutter which mechanically blocks light which is incident onto the imaging element is used together so that the same processing may be performed even by a global shutter manner.

Third Control Example

FIG. 10 is an explanatory view illustrating third driving to match brightness levels in image signals of a pixel of an RG line whose exposure time is short and a pixel of a GB line whose exposure time is long. FIG. 10 illustrates contents of an image signal of a moving image of 60 fps whose gain is changed. In the above-mentioned third driving pattern, a read-out operation of the charge signal is the same as those illustrated in FIGS. 6 and 7, but in this driving pattern, the image signal is amplified for a pixel of the RG line whose exposure time is short. Specifically, when the ratio of the exposure time of the pixel of the RG line and the exposure time of the pixel of the GB line is 1:2, the signal is amplified by an amplifying element which is equipped in the imaging element 51 (see FIG. 1) so as to set a gain of the RG line to be twice higher than a gain of the GB line. That is, in Frame 1 illustrated in FIG. 10, the image signals R1 and Gr1 are amplified so as to be α times higher than the image signals B1 and Gb. "α" is a value which is set according to the ratio of the exposure times.

The signal amplification may be performed in the imaging element 51 or the ADC unit 53 or the image processing unit 65 may amplify the image signal. In such a case, because the image may be formed while interpolating information on different exposure timings, the image quality of the moving image may be further improved.

According to the driving pattern, the exposure time is elongated to improve the sensitivity of detecting the B signal and the brightness level of the signals R and Gr may match with the brightness level of the B signal by adjusting the gains of the signals R and Gr. Therefore, noise of the signal B which is a target of image emphasis is reduced so that a high quality moving image, of which a brightness level for each color is appropriately adjusted, may be obtained.

Fourth Control Example

Next, a fourth driving pattern which expands a dynamic range will be described using a fact that exposure times of the pixel of the RG line and the pixel of the GB line are different from each other.

Figure 11:
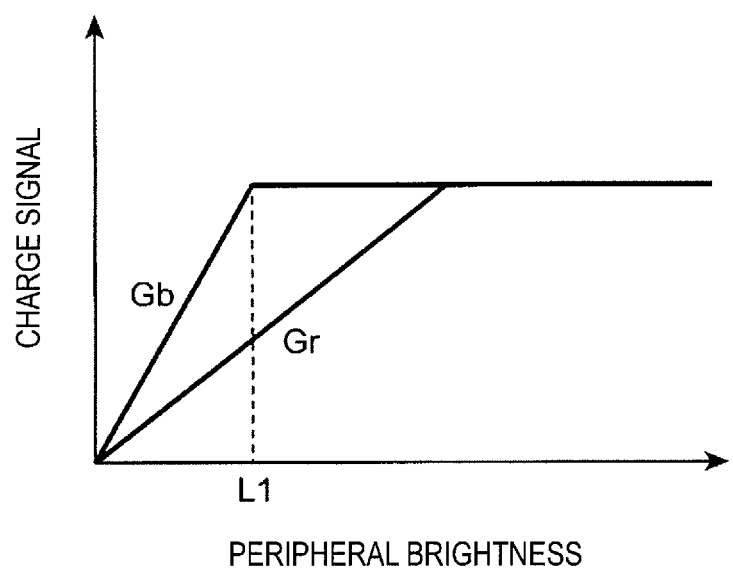
FIG. 11 is a graph illustrating a relationship of an accumulated charge signal of a pixel Gr of an RG line whose exposure time is short and a pixel Gb of a GB line whose exposure time is long with respect to a peripheral brightness.

FIG. 11 is a graph illustrating a relationship of an accumulated charge signal of a pixel Gr of an RG line, of which an exposure time is short and a pixel Gb of a GB line, of which an exposure time is long with respect to a peripheral brightness. When an image is captured with a peripheral brightness L1, the accumulated charge of the pixel Gb is saturated, but the accumulated charge of the pixel Gr is still in a linearly changing region. Therefore, in a range of the peripheral brightness until the accumulated charge of the pixel Gb is saturated, the charge signal of the pixel Gb is used as an image signal of which the dynamic range is 100% and in a range above the peripheral brightness with which the Gb is saturated, the charge signal of the pixel Gb is used to generate an image signal.

For example, when the charge signal of the pixel Gb is twice as large as the charge signal of the pixel Gr after the accumulated charge of the pixel Gb is saturated, the charge signal of the pixel Gr is used as an image signal of which the dynamic range is 200%. Further, when the charge signal of the pixel Gb is three times as large as the charge signal of the pixel Gr, the charge signal of the pixel Gr is used as an image signal of which the dynamic range is 300%

According to the driving pattern, all charge signals from both the pixel Gr and the pixel Gb are used to generate a high quality moving image in which a bright portion without overexposure and a dark portion without under-exposure may be simultaneously reproduced.

In the case of the driving pattern in which the electronic shutter illustrated in FIG. 9 is used together, the ratio of the exposure times of the pixel of the RG line and the pixel of the GB line may be arbitrarily varied and an enlargement factor of the dynamic range may be changed in accordance with the ratio of the exposure times. In this case, the shutter open period of the electronic shutter is adjusted such that the ratio of the exposure times of the pixel of the RG line and the pixel of the GB line is always constant.

Then, for example, when the ratio of the exposure time of the pixel of the GB line to the exposure time of the pixel of the RG line is set to 4:1, an image of which the dynamic range is 400% may be obtained by using the charge signal of the pixel Gr as an image signal of which the dynamic range is 400%.

Fifth Control Example

Next, descriptions will be made on a fifth driving pattern in which with respect to the RG line on which a read-in operation of a charge signal is performed at a frame rate which is twice as long as that on the GB line, image signals of two frames which are consecutive in the time axis are averaged so as to output an image signal at the same frame rate as the GB line.

Figure 12:
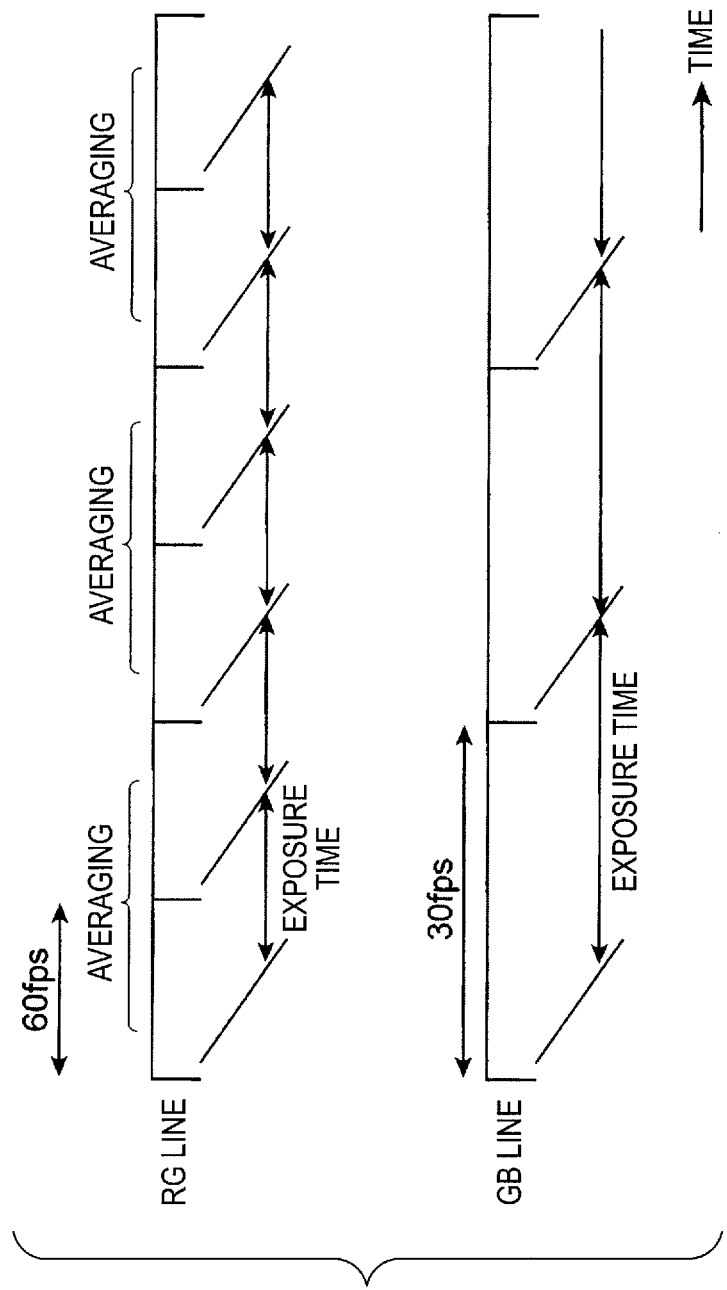
FIG. 12 is an explanatory view illustrating a read-out driving pattern of a charge signal.

FIG. 12 is an explanatory view illustrating a read-out driving pattern of a charge signal. The read-out operation of a charge signal is the same as that illustrated in FIG. 6.

Figure 14:
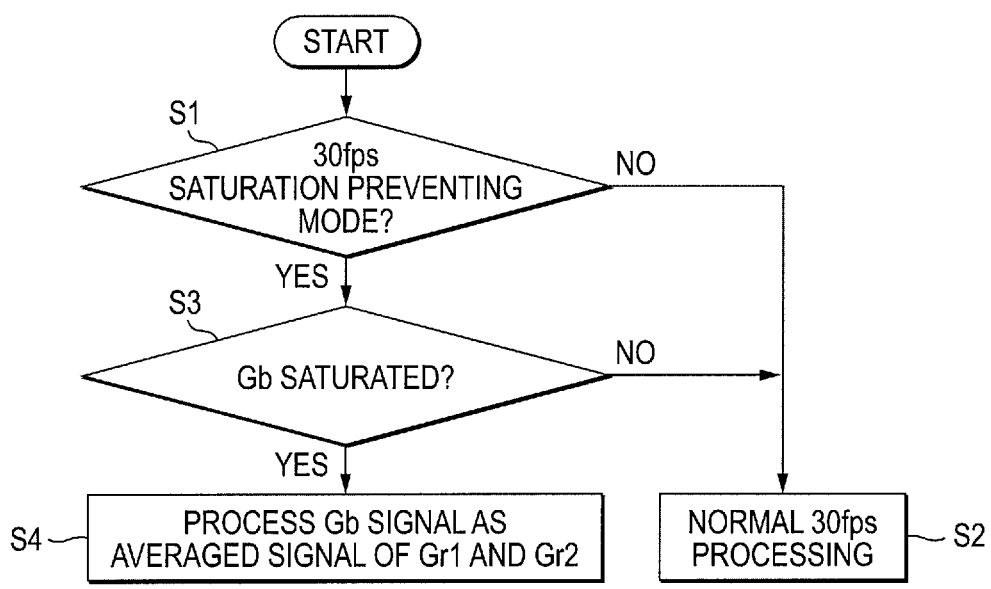
FIG. 14 is a flow chart illustrating a procedure of switching driving patterns.

FIG. 13 illustrates contents of an image signal of a moving image which is generated by information on an image signal obtained from the driving pattern of FIG. 12. The generated moving image is 30 fps. It is assumed that a signal R of Frame 1 of FIG. 14 is a signal obtained by averaging R1 (R1 of FIG. 6) and R2 (R2 of FIG. 6). It is assumed that a Gr signal is a signal obtained by averaging Gr1 (Gr1 of FIG. 6) and Gr2 (Gr2 of FIG. 6), and the Gb signal is a Gb1 signal. Further, it is assumed that a B signal is a B1 signal. Similarly in the subsequent frames, image signals of the RG line are averaged between frame images of two consecutive comas and the averaged signals and the image signals of the GB line are output together.

According to the driving pattern, noise of the image signal of the RG line is reduced by the averaging processing. Further, in cases when it is desired to increase the level of the image signal of the pixel B of the GB line or the image signal is affected by reflective light of light from a high luminous light source, an image signal of the pixel Gb is saturated in some cases. In this case, when an averaged image signal of the pixel Gr of the RG line is used as the signal Gb, a high quality moving image with reduced noise may be obtained. Further, after the averaging processing, the signal may be amplified to adjust the image signal of the pixel B and the brightness level. Further, an addition processing may be performed instead of the averaging processing.

FIG. 14 is a flow chart illustrating a procedure of switching the averaging processing in accordance with the captured image. The imaging control unit 67 illustrated in FIG. 1 sets whether to capture an image with a 30 fps saturation preventing mode illustrated in FIGS. 12 and 13, based on a command from the input unit 17 or a command from the driving control unit 59 of the endoscopic scope 11 or the light source control unit of the light source device 19.

The imaging control unit 67 determines whether the 30 fps saturation preventing mode is set or not (S1) and when the mode is not set, captures an image in with the normal 30 fps mode (for example, capturing a moving image illustrated in FIG. 13) (S2). When the mode is set, the imaging control unit 67 determines whether the image signal of the pixel Gb of the GB line is saturated or not (S3), and when the image signal is not saturated, captures an image in the normal 30 fps mode (S2). When the image signal is saturated, the signal Gb is substituted by averaging the signals Gr1 and Gr2 to perform photography (S4).

When the frame images of two comas are averaged, it is desirable to perform positioning of feature points of the frame images of two comas. An averaged image without being blurred may be generated by performing the positioning of the feature points on the image.

Figure 15:
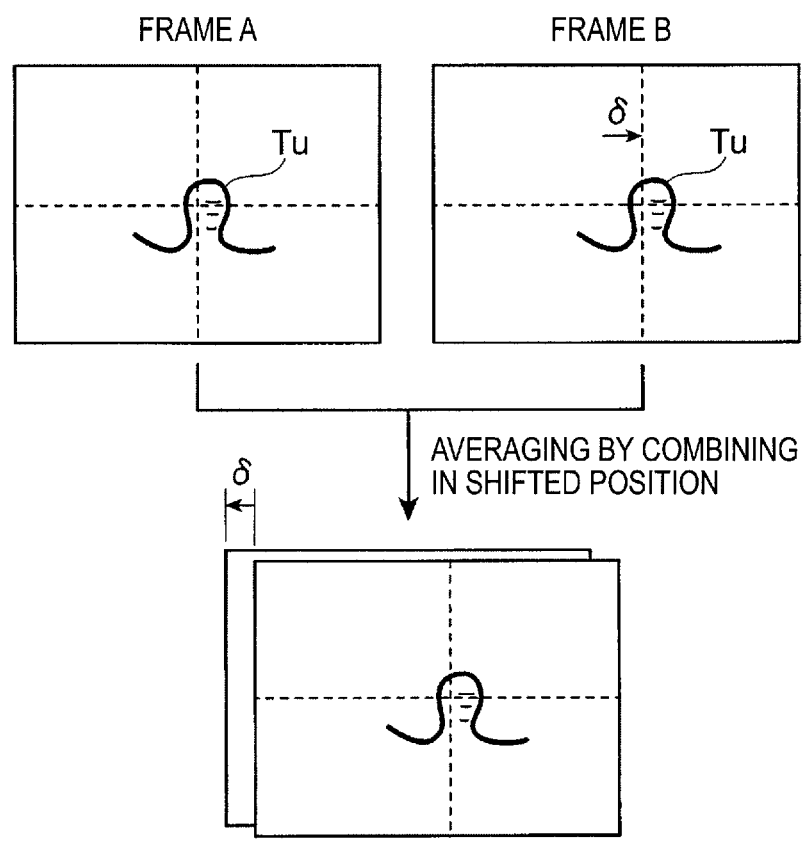
FIG. 15 is an explanatory view illustrating an aspect of performing positioning of feature points.

FIG. 15 illustrates an explanatory view of a state when positioning of feature points is performed. For example, it is assumed that an image of Frame A obtained from the RG line and an image of Frame B obtained from the GB line have feature points which are tumors Tu. When the feature points are deviated from each other by δ in the horizontal direction in Frames A and B, if the signals are combined as they are and the averaging for every pixel is performed, a burred averaged image may be formed. Therefore, the positions of the pixels in the frames A and B are relatively shifted in a direction opposite to the direction of deviation δ. Then, the feature point positions of two frame images become the same image positions. In this shifted position, the pixels are averaged for corresponding positions of the frame images. The detection processing of the feature point may be performed using a known method.

In this case, even if the feature points are located in the different positions between the frames at the time of imaging a moving image, the frame images are averaged after correcting the deviation. Thus, an averaged image with high sharpness may be obtained and hence the quality of the moving image may be improved. Further, frame images to be averaged are not limited to the two comas, and a plurality of arbitrary comas may be allowed. That is, imaging elements may be driven by setting a read-out time interval of the RG line to be m (m is an integer) times as long as a read-out time interval of the GB line and the images may be averaged in m comas which are consecutive in the time axis. In this case, the positioning of the feature points is performed on the images of m comas.

<Application to Endoscopic Device which Obtains Information of Blood Oxygen Saturation Level>

Next, a driving pattern to be applied to an endoscopic device which detects a blood oxygen saturation level will be described. In this endoscopic device, reflective light of illumination light irradiated from a light source unit is imaged by an imaging element, image signals, which correspond to reflective lights having different colors and include an image signal from a pixel B and a pixel R in which an absorption coefficient varies depending on an oxygen saturation level of blood hemoglobin and an image signal from pixels G (Gr and Gb) in which the absorption coefficient does not vary, are obtained, and information on a blood volume and the oxygen saturation level of the blood hemoglobin of the subject is calculated and displayed based on the obtained image signals.

Figure 16:
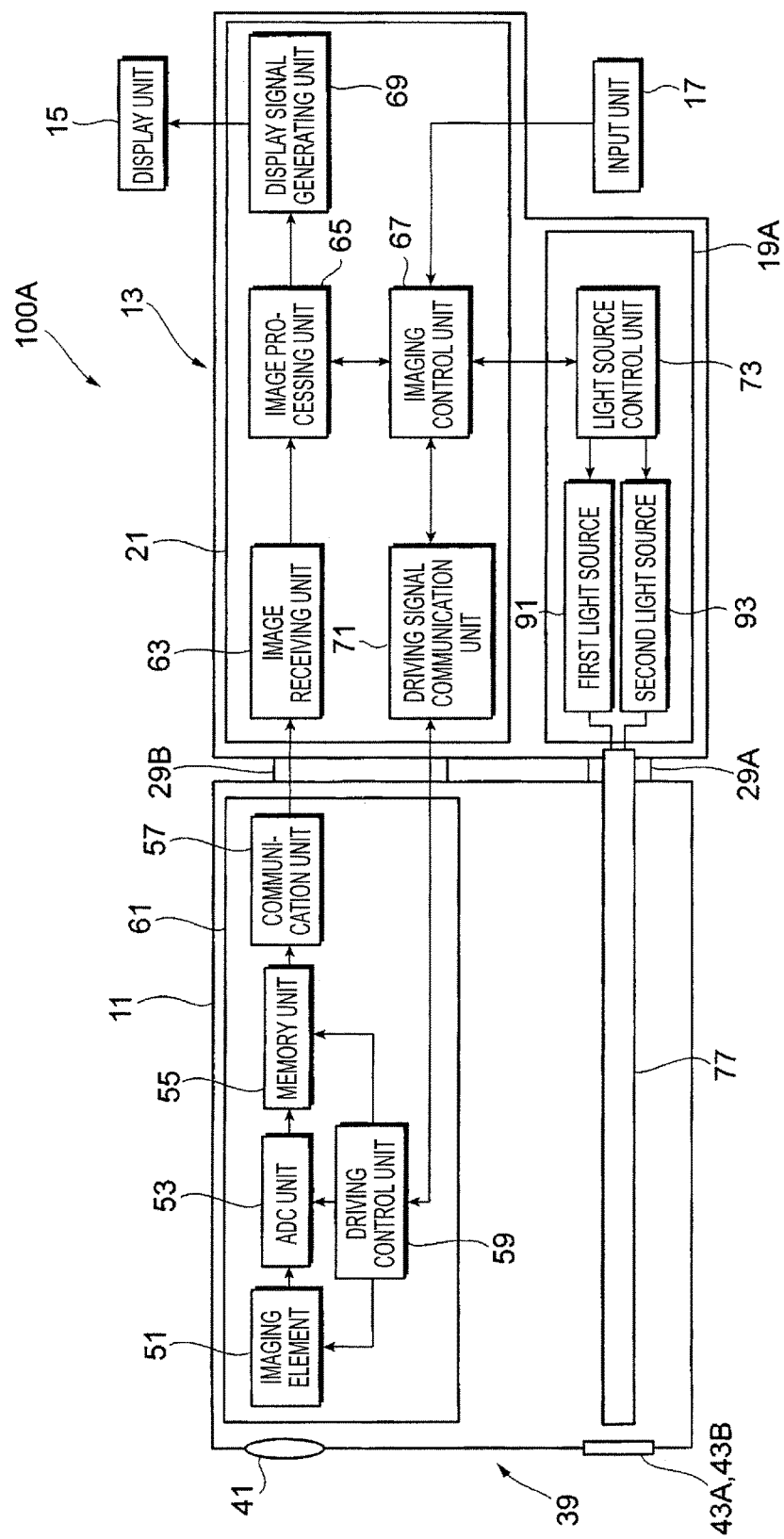
FIG. 16 is a block diagram of an endoscopic device which detects a blood oxygen saturation level.

FIG. 16 illustrates a block diagram of an endoscopic device which detects a blood oxygen saturation level. The configuration of the endoscopic device 100A illustrated in FIG. 16 is the same configuration as the endoscopic device 100 illustrated in FIG. 1, except for the light source device 19. In the following description, the common components are denoted by the same reference numerals, and the descriptions thereof will be omitted or simplified.

A light source device 19A includes a first light source 91 and a second light source 93 having different spectrums. The first light source 91 is a light source obtained by combining a laser light source having a center wavelength of 445 nm and a phosphor and emission light thereof includes a blue light having a center wavelength of 445 nm and emission of green to red phosphors in a wavelength range of approximately 470 to 700 nm. The second light source 93 includes a laser light source having a center wavelength of 473 nm.

As for the blue light of the second light source 93, a center wavelength is preferably 473 nm but the wavelength range may be 460 nm to 480 nm.

Figure 17:
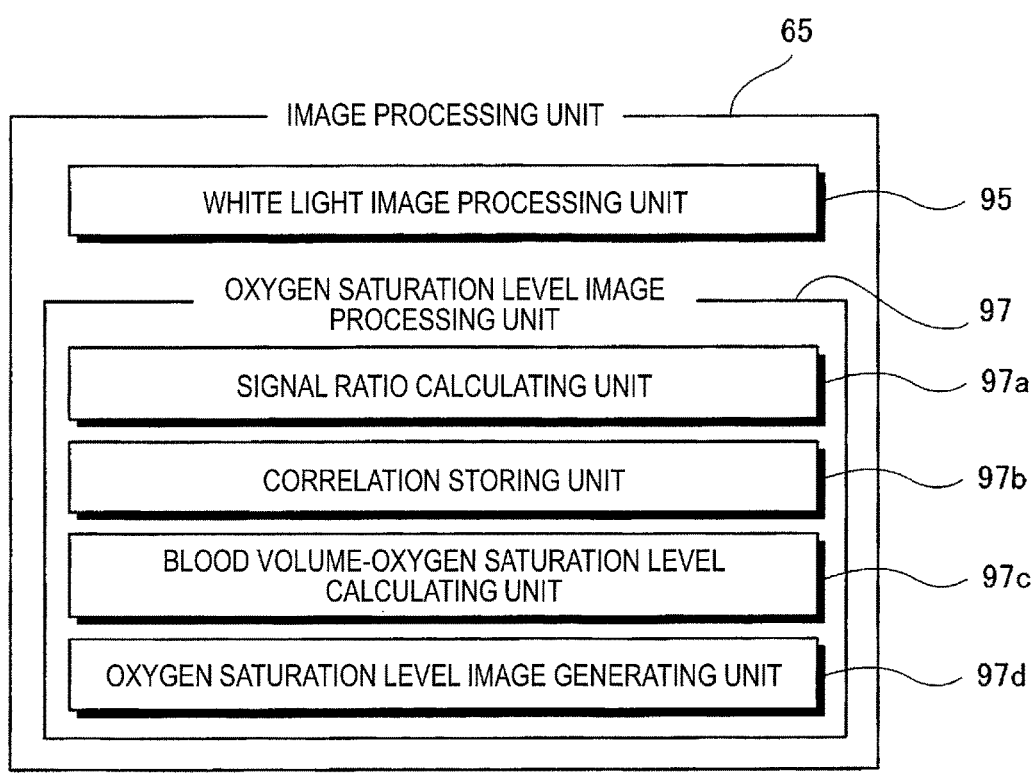
FIG. 17 is a block diagram of an image processing unit of an endoscopic device.

An image processing unit 65 of the endoscopic device 100A, as illustrated in FIG. 17, includes a white light image processing unit 95 and an oxygen saturation level image processing unit 97. The white light image processing unit 95 performs an appropriate image processing on a white light image of an image signal which is input from an endoscopic scope 11 to output a white light image signal in the white light observation mode.

The oxygen saturation level image processing unit 97 calculates information on a blood volume and an oxygen saturation level of a blood hemoglobin of a subject based on an image signal input from the endoscopic scope 11 in the oxygen saturation degree observation mode. An oxygen saturation level image signal is output based on the calculated information on the oxygen saturation level in order to display a distribution of the oxygen saturation level as a pseudo color image. The oxygen saturation level image processing unit 97 includes a signal ratio calculating unit 97a, a correlation storing unit 97b, a blood volume-oxygen saturation level calculating unit 97c, and an oxygen saturation level image generating unit 97d.

The signal ratio calculating unit 97a identifies a vessel area from the image signal input from the endoscopic scope 11 based on a difference of an image signal of a blood vessel part and an image signal of other parts. The signal ratio calculating unit 97a calculates signal ratios S1/S3 and S2/S3, assuming that image signals, which correspond to reflective lights of two narrow band light in a wavelength range where a magnitude relationship of absorbances of reduced hemoglobin and oxygenated hemoglobin is reversed in accordance with the oxygen saturation level of the blood hemoglobin, are S1 and S2 and an image signal which corresponds to a reflective light of one narrow band light in a wavelength range where the absorbances become equal to each other, is as S3, as for pixels in the same position in the blood area.

The correlation storing unit 97b stores the correlation of the signal ratios S1/S3 and S2/S3 and the blood volume and the oxygen saturation level. The correlation refers to a correlation when the blood vessel has an absorbance of the hemoglobin illustrated in FIG. 18 and is obtained by analyzing a plurality of image signals which is accumulated by diagnosis in the past.

Figure 18:
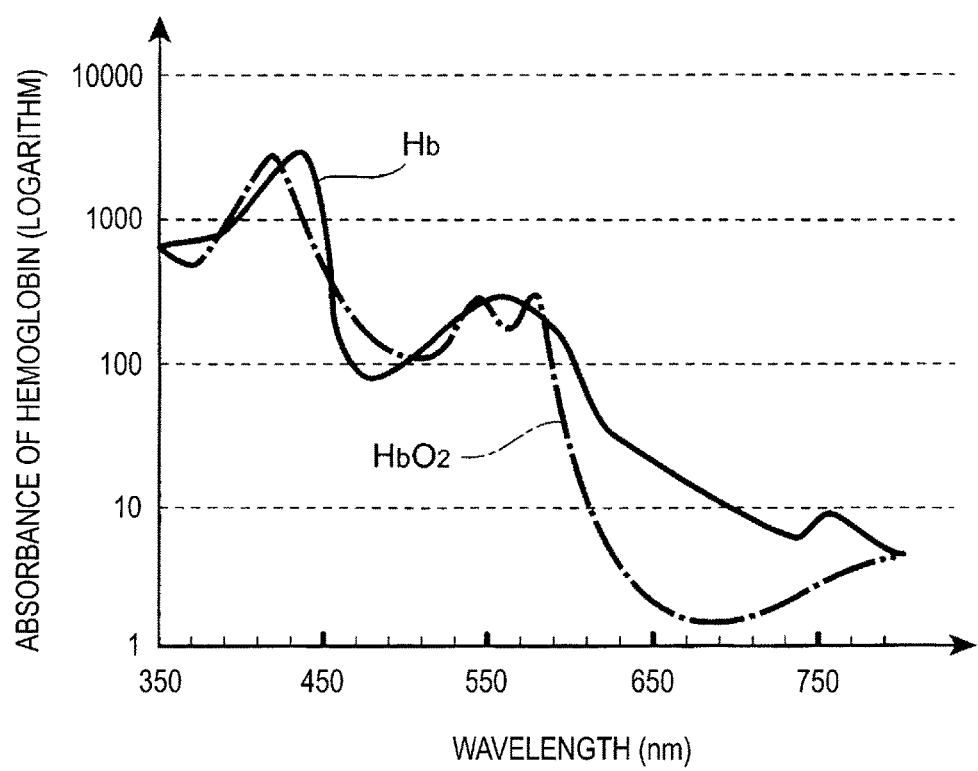
FIG. 18 is a graph illustrating wavelength distribution of an absorbance of hemoglobin.

As illustrated in FIG. 18, the blood hemoglobin has an absorbance characteristic that the absorbance is changed by a wavelength of an irradiated light. The absorbance refers to an amount of light which is absorbed by the hemoglobin. Further, reduced hemoglobin Hb which is not coupled to oxygen and oxygenated hemoglobin $HbO_2$ which is coupled to oxygen have different absorbance characteristics and the absorbances are different from each other, except for an isosbestic point (an intersection point of hemoglobin Hb and $HbO_2$ in FIG. 18) which indicates the same absorbance.

Generally, because the distribution of FIG. 18 changes non-linearly by a portion of a subject to be imaged, it is required to calculate the distribution in advance by actual measurement or light propagation simulation of a living tissue.

Figure 19:
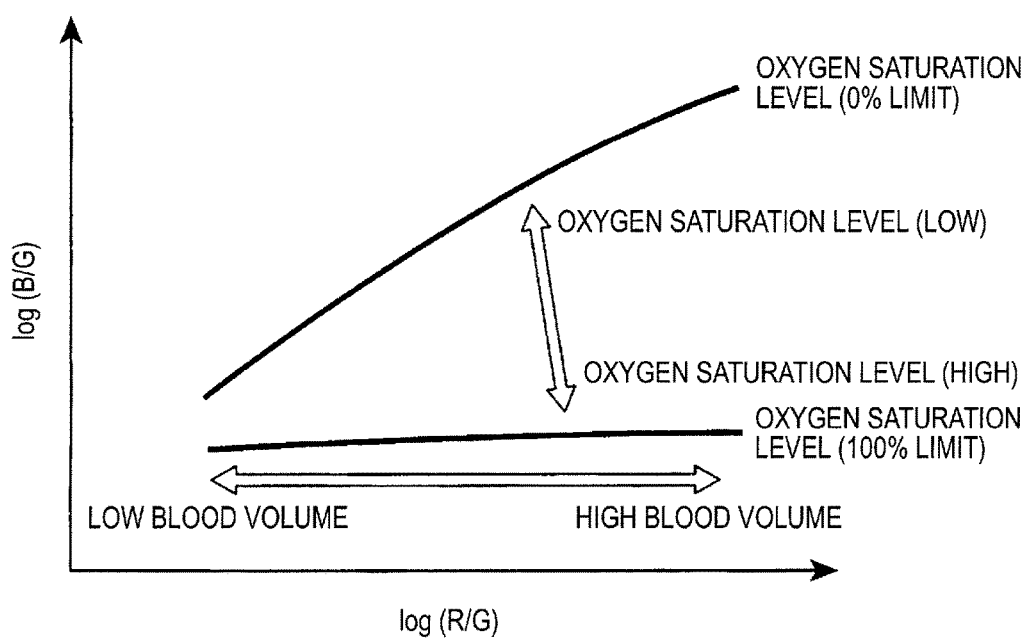
FIG. 19 is a graph illustrating a correlation of signal ratios B/G and R/G and a blood volume, and an oxygen saturation level.

Here, the image signal S1 corresponds to the R signal, the image signal S2 corresponds to the B signal, and the image signal S3 corresponds to the G signal. FIG. 19 is a graph illustrating a correlation of signal ratios B/G and R/G and a blood volume, and an oxygen saturation level. The horizontal axis of the graph is log(R/G) and the vertical axis is log(B/G) in which the signal ratio R/G (a second signal ratio) corresponds to a signal ratio S1/S3 and the signal ratio B/G (a first signal ratio) corresponds to a signal ratio S2/S3. As illustrated in this graph, the value of the signal ratio R/G varies depending on the blood volume and increases as the blood volume increases. Further, the value of the signal ratio B/G varies depending on both the blood volume and the oxygen saturation level. That is, the value of the signal ratio B/G increases as the blood volume increases and also increases as the oxygen saturation level decreases.

The blood volume-oxygen saturation level calculating unit 97c calculates the blood volume and the oxygen saturation level corresponding to the signal ratios R/G and B/G calculated in the signal ratio calculating unit 97a based on the correlation stored in the correlation storing unit 97b.

The oxygen saturation level image generating unit 97d includes a color table in which color information is allocated according to a height of the oxygen saturation level. The color table may be switched by an instruction input from the input unit 17 (see FIG. 1) and for example, is selected in accordance with a portion to be observed, such as stomach, duodenum, or small intestine. The oxygen saturation level image generating unit 97d identifies color information corresponding to the oxygen saturation level calculated in the blood volume-oxygen saturation level calculating unit 97c using the color table. When the color information for all pixels in the blood region is identified, the oxygen saturation level image generating unit 97d reflects the color information onto the image signal of a white light image so as to generate an oxygen saturation level image signal to which the oxygen saturation level of the blood hemoglobin is reflected (pseudo color is represented).

The image signal processed in the image processing unit 65 is sent to the imaging control unit 67 and is changed into an endoscopic observation image to be displayed on the display unit 15 together with various information in the imaging control unit 67. Further, if necessary, the image signal is stored in the storing unit which is configured by a memory or a storage device.

Next, a method of calculating the blood volume and the oxygen saturation level will be described.

When light is incident into a mucosal tissue of a subject, a part of the light is absorbed by a blood vessel portion and the remaining light which is not absorbed returns as reflective light. In this case, as a depth of the blood vessel is increased, the light is significantly affected by the scattering from a tissue on the blood vessel.

However, a light in a wavelength range of 470 to 700 nm has a property that has a low scattering coefficient in the mucosal tissue and a low wavelength dependency. When the light in this wavelength range is used as illumination light, it is possible to obtain blood information including information on a blood volume and an oxygen saturation level while reducing influence of the depth of the blood vessel. The endoscopic device 100A calculates an oxygen saturation level of the blood hemoglobin using image signals (details thereof will be described below) corresponding to three or more different reflective lights including reflective lights in two or more wavelength ranges in which the absorption coefficient varies depending on the oxygen saturation level of the blood hemoglobin and a reflective light in one or more wavelength ranges in which the absorption coefficient does not vary.

Here, the three points may be indicated from wavelength dependency of the absorption coefficient of the blood hemoglobin.

An absorption coefficient significantly varies according a change of the oxygen saturation level in the vicinity of a wavelength of 470 nm (for example, a wavelength range of B of 470 nm (center wavelength)±10 nm).

When averaging is performed in a wavelength range of G of 540 nm to 580 nm, the absorption coefficient is hardly affected by the oxygen saturation level.

In a wavelength range of R of 590 to 700 nm, it may be seen that the absorption coefficient significantly varies by the oxygen saturation level. However, because the value of the absorption coefficient is very small, the absorption coefficient is hardly affected by the oxygen saturation level.

The following two properties are observed from a reflection spectrum of a mucous membrane:

It may be considered that influence of hemoglobin is little in the wavelength range of R. However, because absorption occurs in the wavelength range of G, as the blood volume (corresponding to a size of a blood vessel or a density of a blood vessel) increases, the difference between the reflectance in the wavelength range of G and the reflectance in the wavelength range of R increases.

The difference between the reflectance in the vicinity of a wavelength 470 nm and the reflectance in the wavelength range of G increases as the oxygen saturation level decreases and also increases the blood volume increases.

That is, the value of the signal ratio B/G between the image signal B of the pixel B and the image signal G of the pixel G varies depending on both the oxygen saturation level and the blood volume and the value of the signal ratio R/G between the image signal G of the pixel G and the image signal R of the pixel R varies mainly depending on only the blood volume. Therefore, using this property, the oxygen saturation and the blood volume are separated from a spectral image in three wavelength ranges including the vicinity of the wavelength of 470 nm, and the wavelength ranges of G and R so as to precisely calculate the values. The graph of FIG. 19 was prepared based on this in which FIG. 19 represents a correlation of signal ratios B/G and R/G, a blood volume, and an oxygen saturation level.

Next, descriptions will be made on image signals corresponding to three or more types of reflective lights having different wavelength ranges including reflective lights in two or more wavelength ranges in which the absorption coefficient varies depending on the oxygen saturation level of the blood hemoglobin and reflective lights in one or more wavelength ranges in which the absorption coefficient does not vary.

Lights emitted from the first light source 91 are a blue light having a center wavelength of 445 nm and a light having a wavelength range of approximately 470 to 700 nm which is emitted from the phosphor and respective color image signals are detected from the pixel R, the pixel G (Gr, Gb), and the pixel B of the imaging element. Meanwhile, light emitted from the second light source 93 desirably includes a light having a center wavelength of 473 nm, and the reflective light from the subject is detected from the pixel B of the imaging element.

Figure 20:
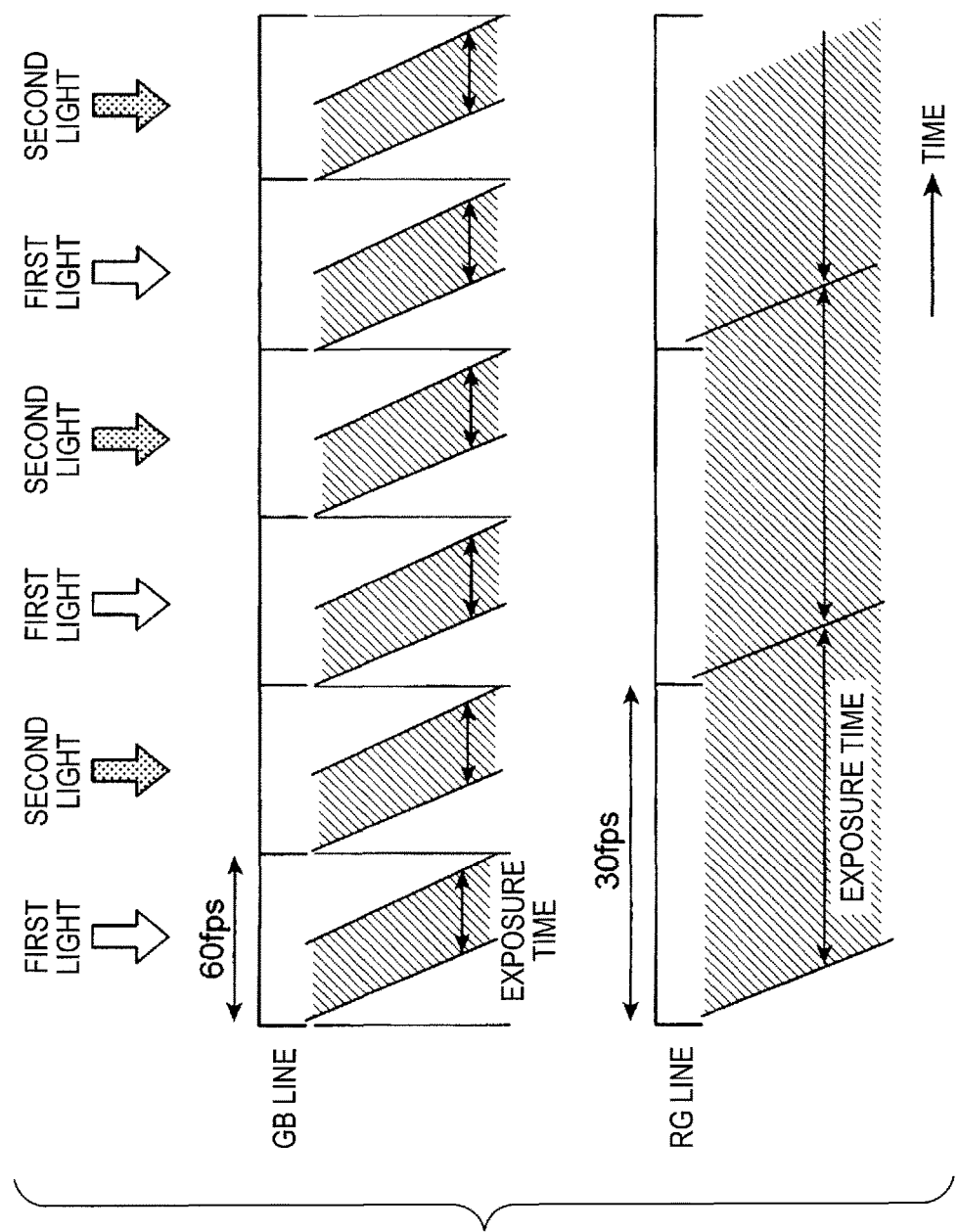
FIG. 20 is an explanatory view illustrating a read-out driving pattern of a charge signal.

FIG. 20 illustrates an explanatory view of a read-out driving pattern of a charge signal. In this driving pattern, the GB line reads out the charge signal at 60 fps and the RG line reads out the charge signal at 30 fps. The illumination light from the first light source 91 and the illumination light from the second light source 93 are switched into a predetermined pattern to be irradiated in synchronization with the read-out timing of the charge signal of the GB line.

Figure 21:
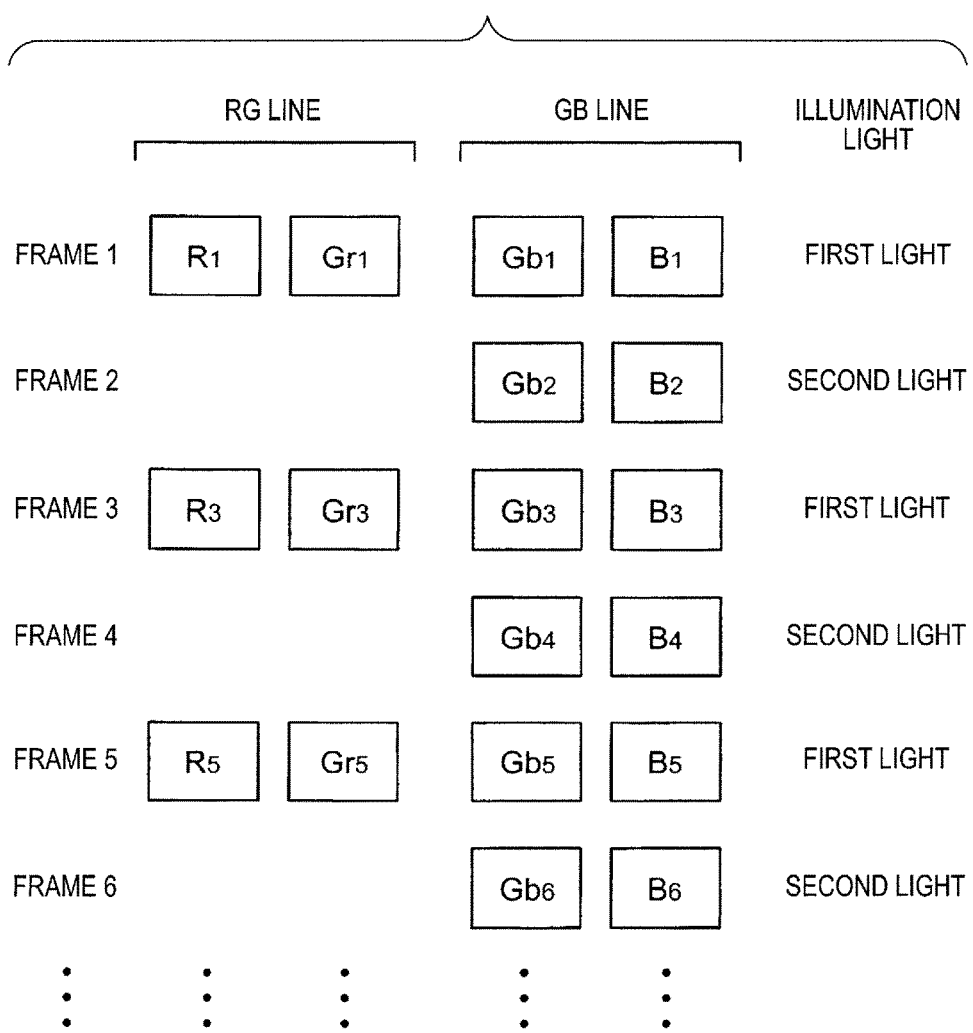
FIG. 21 is an explanatory view illustrating transition of image information obtained by the driving pattern of FIG. 20.

Transition of the image information obtained by the driving pattern is schematically illustrated in FIG. 21. During the period of Frame 1, image signals R1 and Gr1 of the RG line and image signals Gb1 and B1 of the GB line may be obtained as a reflective light by the first light from the first light source 91. During the period of Frame 2, image signals Gb2 and B2 of the GB line may be obtained as a reflective light by the second light from the second light source 93. During the period of Frame 3, image signals R2 and Gr2 of the RG line and image signals Gb3 and B3 of the GB line may be obtained similarly to Frame 1.

FIG. 22 illustrates contents of R, G, and B signals as an example to calculate information of a blood volume and an oxygen saturation level of blood hemoglobin of a subject which are obtained from image information illustrated in FIG. 21. In Frame 1, it is assumed that R1 of the RG line is an R signal and Gr1 is a G signal. In Frame 2, it is assumed that B2 of the GB line is a B signal. In Frame 3, it is assumed that R2 of the RG line is an R signal and Gr2 is a G signal. In Frame 4, it is assumed that B4 of the GB line is a B signal.

When the values of the signal ratios R1/Gr1 and B2/Gr1 are calculated from Frames 1 and 2 and the values of the signal ratios R2/Gr2 and B4/Gr2 are calculated from Frames 3 and 4, information on the blood volume and the oxygen saturation level of the blood hemoglobin of the subject may be obtained at every frame update of 30 fps. Further, when a processing of calculating values of the signal ratios R2/Gr2 and B2/Gr2 from the frames 2 and 3 is added, the information may be generated at 60 fps. Further, when the second light source 93 irradiates a G light component and an R light component in addition to the light having the center wavelength of 473 nm, Gb1 may be used for generating the G signal, in addition to Gr1.

According to this driving pattern, information on the blood volume and the oxygen saturation level of the blood hemoglobin of the subject may be calculated from the RGB signals. Further, when an image signal from the pixel Gr of the RG line, of which the exposure time is long, is used as the G signal, high precise information with reduced noise may be obtained. Further, the processing of the signal ratio is an example and the processing of the signal ratio is not limited thereto.

While the information on the blood volume and the oxygen saturation level of the blood hemoglobin of the subject is calculated, an observation image under white light illumination may be output as a moving image. In that case, from the image information illustrated in FIG. 21, R1 of Frame 1 is used as the R signal of the frame image and any of Gr1, Gb1, and Gb2 of Frame 1 or a signal obtained by a combination thereof (e.g., addition, averaging, or weighted addition) is used as the G signal, and any of B1 of Frame 1 and B2 of Frame 2 or a signal obtained by a combination thereof as described above is used as the B signal.

Then, even when the spectrums of the illumination lights are different from each other, image signals R1, Gr1, Gr2, B1, and B2 obtained from the imaging element are appropriately combined to obtain an observation moving image under the white illumination.

The present invention is not limited to the above-described embodiments, and it is anticipated by the present invention that a person skilled in the art may combine, change or apply respective components of the embodiment based on the description of the specification and a known technology, which is included in the scope to be protected.

For example, a color which increases sensitivity is not limited to the above-mentioned specific colors and sensitivity for reflective lights of other arbitrary colors may be increased. For example, as in the above description, the exposure time for a pixel of the RG line is set to be longer than the exposure time for a pixel of the BG line so that the sensitivity of the pixel R may be increased.

As described above, the description of embodiments discloses the following matters.

(1) It is a method of driving a MOS type imaging element in which pixels having sensitivities for different colors are arranged two-dimensionally, in which the imaging element has at least two types of read-out lines having different pixel arrangements to read out a charge signal of the pixels, and the method includes driving such that a read-out time interval of a charge signal of at least one type of read-out line among the read-out lines is longer than a read-out time interval of another type of read-out line and a charge accumulating period of each pixel of the one type of read-out line is longer than a charge accumulating period of each pixel of said another type of read-out line.

(2) It is the driving method of (1), in which the charge accumulating period is a period from a read-out timing of the charge signal to a next read-out timing.

(3) It is the driving method of (1), in which the charge accumulating period is a shutter open period of an electronic shutter.

(4) It is the driving method of any one of (1) to (3), in which the charge accumulating period of the pixel of the one type of read-out line is twice as long as the charge accumulating period of the pixel of said another type of read-out line.

(5) It is the driving method of any one of (1) to (4), in which the read-out lines are two types of read-out lines including a first read-out line, in which pixels B having sensitivity for a blue light and pixels Gb having sensitivity for a green light are repeatedly arranged, and a second read-out line, in which pixels R having sensitivity for a red light and pixels Gr having sensitivity for a green light are repeatedly arranged, and the first read-out line is the one type of read-out line and the second read-out line is said another type of read-out line.

(6) It is the driving method of any one of (1) to (4), in which the read-out lines are two types of read-out lines including a first read-out line, in which pixels B having sensitivity for a blue light and pixels Gb having sensitivity for a green light are repeatedly arranged, and a second read-out line, in which pixels R having sensitivity for red light and pixels Gr having sensitivity for green light are repeatedly arranged, and the first read-out line is said another type of read-out line and the second read-out line is the one type of read-out line.

(7) It is an imaging device including: a MOS type imaging element in which pixels having sensitivities for different colors are arranged two-dimensionally; and a driving control unit which drives the imaging element by the driving method of the imaging element of any one of (1) to (6).

(8) It is the imaging device of (7), further including: an image processing unit which generates an image signal obtained by combining an image signal of each pixel of the one type of read-out line with an image signal of each pixel of said another type of read-out line.

(9) It is the imaging device of (8), in which, when driving the imaging element, the driving control unit sets a read-out time interval of the one type of read-out line to be m times as long as a read-out time interval of said another type of read-out line where m is an integer, and the image processing unit averages image signals from pixels having sensitivity for different colors which are obtained from said another type of read-out line at m comas which are consecutive in a time axis and generates image signals of one frame using the averaged image signals and the image signals from the pixels having sensitivity for different colors which are obtained from the one type of read-out line.

(10) It is the imaging device of (9), in which the image processing unit performs the averaging after matching positions of same feature points which are included in the images of the m comas which are obtained from said another type of read-out line with same image positions.

(11) It is the imaging device of (9) or (10), in which the image processing unit amplifies the image signals obtained from said another type of read-out line with a higher gain than the image signals obtained from the one type of read-out line.

(12) It is the imaging device of (9) or (10), in which the image processing unit generates an image signal of which a dynamic range is expanded using both an image signal obtained from the one type of read-out line and the image signal obtained from said another type of read-out line, for pixels which have color sensitivity for the same color and are included in both the one type of read-out line and said another type of read-out line.

(13) It is the imaging device of any one of (7) to (12), further including: a light source unit which switches and irradiates a plurality of types of illumination lights having different spectrums by a predetermined pattern in synchronization with a read-out timing of a charge signal of each pixel for said another type of read-out line.

(14) It is an endoscopic device, including the imaging device of (13).

What is claimed is:

1. A method of driving a MOS type imaging element in which pixels having sensitivities for different colors are arranged two-dimensionally,
wherein the imaging element has at least two types of read-out lines having different pixel arrangements to read out a charge signal of the pixels, and
the read-out lines are two types of read-out lines including a first read-out line, in which pixels B having sensitivity for a blue light and pixels Gb having sensitivity for a green light are repeatedly arranged, and a second read-out line, in which pixels R having sensitivity for a red light and pixels Gr having sensitivity for a green light are repeatedly arranged,
the method comprising:
driving such that a read-out time interval of a charge signal of at least one type of read-out line among the read-out lines is longer than a read-out time interval of another type of read-out line and a charge accumulating period of each pixel of the one type of read-out line is longer than a charge accumulating period of each pixel of said another type of read-out line,
wherein driving the first read-out line includes reading out both pixels B and pixels Gb and driving the second read-out line includes reading out both pixels R and pixels Gr;
switching a plurality of types of illumination lights having different spectrums by a predetermined pattern in synchronization with a read-out timing of a charge signal of each pixel for said another type of read-out line; and
calculating a blood volume and an oxygen saturation level of a blood hemoglobin of a subject based on a first signal ratio between a signal output from the pixels B of the first read-out line and a signal output from the pixels Gb of the first read-out line, a second signal ratio between a signal output from the pixels R of the second read-out line and a signal output from the pixels Gr of the second read-out line, and a predetermined correlative relationship between the first signal ratio, the second signal ratio and the blood volume and the oxygen saturation level of a blood hemoglobin of a subject, wherein each read-out line of the at least one type of read-out line has a first read-out time interval, and wherein each read-out line of the another type of read-out line has a second read-out time interval.

2. The driving method of claim 1, wherein the charge accumulating period is a period from a read-out timing of the charge signal to a next read-out timing.

3. The driving method of claim 1, wherein the charge accumulating period is a shutter open period of an electronic shutter.

4. The driving method of claim 1, wherein the charge accumulating period of the pixel of the one type of read-out line is twice as long as the charge accumulating period of the pixel of said another type of read-out line.

5. The driving method of claim 1, wherein
the first read-out line is the one type of read-out line and the second read-out line is said another type of read-out line.

6. The driving method of claim 1, wherein
the first read-out line is said another type of read-out line and the second read-out line is the one type of read-out line.

7. The method of claim 1, further comprising:
generating an image signal obtained by combining an image signal of each pixel of the one type of read-out line with an image signal of each pixel of said another type of read-out line.

8. The method of claim 7, further comprising:

setting a read-out time interval of the one type of read-out line to be m times as long as a read-out time interval of said another type of read-out line where m is an integer, and averaging image signals from pixels having sensitivity for different colors which are obtained from said another type of read-out line at m comas which are consecutive in a time axis and generating image signals of one frame using the averaged image signals and the image signals from the pixels having sensitivity for different colors which are obtained from the one type of read-out line.

9. The method of claim 8, wherein the averaging is performed after matching positions of same feature points which are included in the images of the m comas which are obtained from said another type of read-out line with same image positions.

10. The method of claim 8, wherein the image signals obtained from said another type of read-out line is amplified with a higher gain than the image signals obtained from the one type of read-out line.

11. The method of claim 8, further comprising:

generating an image signal of which a dynamic range is expanded using both an image signal obtained from the one type of read-out line and the image signal obtained from said another type of read-out line, for pixels which have color sensitivity for the same color and are included in both the one type of read-out line and said another type of read-out line.

* * * * *